(12) United States Patent
Ohta et al.

(10) Patent No.: US 9,084,817 B2
(45) Date of Patent: Jul. 21, 2015

(54) ORAL PREPARATION COMPRISING SPECIFIC ORGANIC ACID, AND METHOD FOR IMPROVEMENT IN ELUTION PROPERTY AND CHEMICAL STABILITY OF ORAL PREPARATION

(75) Inventors: Kotoe Ohta, Kamakura (JP); Satoshi Minakami, Kamakura (JP); Hiroyuki Tokumitsu, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 702 days.

(21) Appl. No.: 12/600,021

(22) PCT Filed: May 20, 2008

(86) PCT No.: PCT/JP2008/059196
§ 371 (c)(1),
(2), (4) Date: Dec. 14, 2009

(87) PCT Pub. No.: WO2008/143240
PCT Pub. Date: Nov. 27, 2008

(65) Prior Publication Data
US 2010/0215750 A1    Aug. 26, 2010

(30) Foreign Application Priority Data
May 21, 2007   (JP) ................................. 2007-133854

(51) Int. Cl.
*A61K 47/12*     (2006.01)
*A61K 47/18*     (2006.01)
(Continued)

(52) U.S. Cl.
CPC ................ *A61K 47/12* (2013.01); *A61K 9/145* (2013.01); *A61K 9/2013* (2013.01);
(Continued)

(58) Field of Classification Search
None
See application file for complete search history.

(56) References Cited

U.S. PATENT DOCUMENTS 6,372,755 B2   4/2002  Hanamura et al.
7,718,664 B2 * 5/2010  Izumimoto et al. ........... 514/282
(Continued)

FOREIGN PATENT DOCUMENTS

EP    1 736 157 A1    12/2006
JP    2006-509772 A    3/2006
(Continued)

OTHER PUBLICATIONS

Office Action dated May 31, 2012 for Australian Application No. 2008254038.
(Continued)

*Primary Examiner* — Bethany Barham
*Assistant Examiner* — Barbara Frazier
(74) *Attorney, Agent, or Firm* — Birch, Stewart, Kolasch & Birch, LLP

(57) ABSTRACT

A chemically stable oral preparation with an excellent dissolution property comprising as an effective ingredient a specific morphinan derivative or a pharmaceutically acceptable acid addition salt thereof is disclosed. The oral preparation according to the present invention comprises a specific morphinan derivative or a pharmaceutically acceptable acid addition salt thereof as an effective ingredient and an organic acid, wherein 1 g of said organic acid requires not less than 30 mL of water to dissolve in at 20° C. The method for improving dissolution property and chemical stability of an oral preparation according to the present invention comprises incorporating an organic acid in the oral preparation comprising as an effective ingredient a specific morphinan derivative or a pharmaceutically acceptable acid addition salt thereof, wherein 1 g of said organic acid requires not less than 30 mL of water to dissolve in at 20° C.

6 Claims, 1 Drawing Sheet

(51) Int. Cl.
  *A61K 9/20* (2006.01)
  *A61K 9/48* (2006.01)
  *A61K 9/14* (2006.01)
  *A61K 31/485* (2006.01)
  *C07D 489/02* (2006.01)
  *A61K 9/08* (2006.01)
  *A61K 9/28* (2006.01)

(52) U.S. Cl.
  CPC ............ *A61K 9/4858* (2013.01); *A61K 31/485* (2013.01); *A61K 47/183* (2013.01); *C07D 489/02* (2013.01); *A61K 9/08* (2013.01); *A61K 9/205* (2013.01); *A61K 9/2009* (2013.01); *A61K 9/2018* (2013.01); *A61K 9/282* (2013.01); *A61K 9/2866* (2013.01)

(56) References Cited

U.S. PATENT DOCUMENTS

2003/0229111 A1* 12/2003 Oshlack et al. ............... 514/282
2004/0102476 A1   5/2004 Chan et al.
2005/0182115 A1*  8/2005 Hisamatsu et al. ........... 514/381
2007/0259908 A1* 11/2007 Fujii et al. ..................... 514/292
2007/0299100 A1  12/2007 Izumimoto et al.
2009/0111843 A1   4/2009 Kawai et al.

FOREIGN PATENT DOCUMENTS

| WO | WO-99/02158 A1 | 1/1999 |
| WO | WO-2005/094826 A1 | 10/2005 |
| WO | WO-2006/049248 A1 | 5/2006 |
| WO | WO-2007/055184 A1 | 5/2007 |

OTHER PUBLICATIONS

Search Report dated Nov. 12, 2012 for European Application No. 08 75 2992.

* cited by examiner

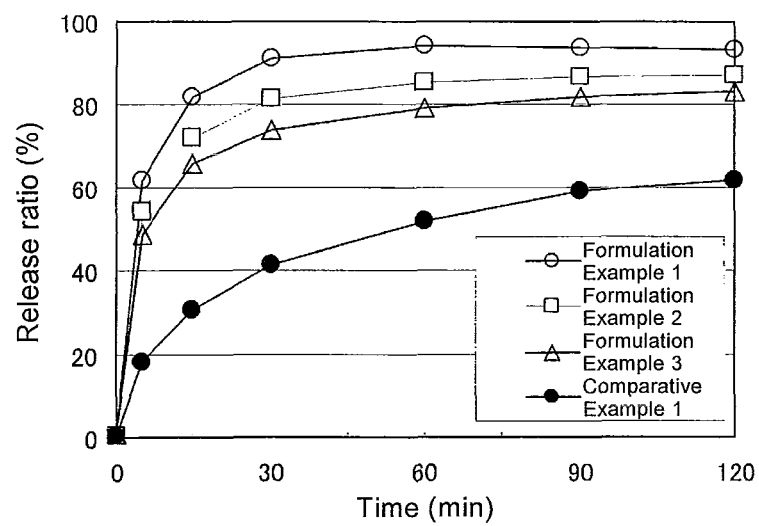
[......1]

ORAL PREPARATION COMPRISING SPECIFIC ORGANIC ACID, AND METHOD FOR IMPROVEMENT IN ELUTION PROPERTY AND CHEMICAL STABILITY OF ORAL PREPARATION

TECHNICAL FIELD

The present invention relates to chemically stable oral preparations having high dissolution property, comprising a specific organic acid and as an effective ingredient a morphinan derivative having a nitrogen-containing heterocyclic group or a pharmaceutically acceptable acid addition salt thereof.

BACKGROUND ART

It is disclosed that specific morphinan derivatives having a nitrogen-containing cyclic group or pharmaceutically acceptable acid addition salts thereof, which have a remarkable therapeutic or prophylactic effect against pollakiuria or urinary incontinence, antipruritic effect, analgesic effect, and therapeutic or prophylactic effect against functional bowel disorder, are useful as a therapeutic agent for pollakiuria, antipruritic, analgesic and therapeutic or prophylactic agent for functional bowel disorder (see, e.g., Patent Literatures 1, 2, 3 and 10). However, morphinan derivatives are known to be chemically unstable to light, heat or oxygen (see, e.g., Patent Literature 4), and actually it was confirmed that morphinan derivatives described in Patent Literatures 1 to 3 are also unstable. Therefore, it has been required to develop remedies with a good stability to ensure quality. In addition, the specific morphinan derivatives mentioned above are much slightly soluble in water, and have a problem in the dissolution property particularly in the neutral region. Thus, it has been required to develop remedies with an improved dissolution property in the neutral region as well as a good chemical stability to ensure stable absorption.

As a method for improving the dissolution property of various morphinan derivatives including morphine, a method in which the active ingredient is dissolved in oil or a solubilizer such as polyethylene glycol or surfactant (e.g., Patent Literature 5), and a method in which a remedy is prepared as a composition comprising a nonionic solubilizer, lipophilic antioxidant and aqueous solvent (e.g., Patent Literature 6) have been reported. However, although Patent Literature 5 demonstrates that the active ingredients show a good dissolution property even after 6-month storage, it does not describe the data of chemical stability such as a change in the amount of decomposition products and the like. In Patent Literature 6, although it describes the effect of antioxidants on solubility and stability, the oral administration form is restricted to solutions or gels, and solid formulations such as tablets and capsules are not described. Moreover, the two literatures do not disclose that the dissolution property can be improved by addition of a specific organic acid according to the present invention.

As a method for improving the dissolution property of basic remedies, a method in which acidic compounds such as organic acids are added thereto, a method in which the dissolution rate is increased by pulverizing active substances with a grinder to increase the surface area, or the solid dispersion method in which the active substances are dispersed in a polymer molecule such as polyethylene glycol or polyvinylpyrrolidone is generally used. However, it is known that pulverization not merely increases surface area of particles, but strongly affects on reactivity and stability of the solid, and the problem that destabilization occurs concurrently with improvement of the dissolution property has been pointed out. It has been also reported that, in the solid dispersion method, many amorphous particles of solid dispersions are often generated and that destabilization occurs due to the high surface energy of the amorphous particles (e.g., Patent Literature 1). Thus, it is a very difficult problem to provide a chemically stable preparation with a high dissolution property containing a poorly soluble, unstable compound.

On the other hand, as a method for stabilizing various morphinan derivatives including morphine, a method in which a basic component is added to morphine (e.g., Patent Literature 7), a method in which naloxone is combined with an antioxidant such as sodium thiosulfate or tocopherol (e.g., Patent Literature 8), and a method in which an antioxidant such as sodium thiosulfate or propyl gallate is added to morphinan derivatives to stabilize the preparation (e.g., Patent Literature 4) have been disclosed.

With respect to the effect of addition of organic acids on the chemical stability of morphinan derivatives, stabilized oral preparations comprising naloxone in combination with ascorbic acid and the like (e.g., Patent Literature 8), stabilization by adding an organic acid to naltrexone hydrochloride (e.g., Patent Literature 9), and stabilization by adding ascorbic acid, erythorbic acid or citric acid to morphinan derivatives (e.g., Patent Literature 4) have been reported. However, none of these publications describes the solubility and the stabilizing effect of the organic acids to be added. In fact, it has been reported that stability is decreased when citric acid and tartaric acid are added to morphine (e.g., Patent Literature 7).

Thus, these known techniques do not give the slightest suggestion of adding a specific organic acid to the above-mentioned specific morphinan derivatives having a nitrogen-containing heterocyclic group or a phainiaceutically acceptable acid addition salt thereof in order to provide remedies with an excellent dissolution property and chemical stability.
Non-patent Literature 1: Mitsuru HASHIDA eds., "Designing and Evaluation of Oral Preparations", 1st Edition, Jihou Co., Ltd., Feb. 10, 1995, p. 167-179
Patent Literature 1: WO 2004/033457
Patent Literature 2: WO 2005/094826
Patent Literature 3: WO 2006/049248
Patent Literature 4: WO 99/02158
Patent Literature 5: JP 2960169 B
Patent Literature 6: WO 2004/026231
Patent Literature 7: JP 2-160719 A
Patent Literature 8: WO 98/35679
Patent Literature 9: JP 2005-531515 A
Patent Literature 10: WO 2007/055184

DISCLOSURE OF THE INVENTION

Problems which the Invention Tries to Solve

An objection of the present invention is to provide a chemically stable oral preparation with an excellent dissolution property comprising as an effective ingredient a specific morphinan derivative or a pharmaceutically acceptable acid addition salt thereof.

Means for Solving the Problem

Since a preliminary experiment revealed that morphinan derivatives having a nitrogen-containing heterocyclic group represented by the Formula (I) below are chemically unstable to light, heat and oxygen, the present inventors tried preparing various formulations selecting compatible additives and production methods based on the prior art information. However, it was proved that such common techniques are not effective enough to ensure stability and dissolution property. On the other hand, the dissolution property could be improved to some extent by adding an organic acid to the basic compound morphinan derivatives having a nitrogen-containing heterocyclic group represented by the Formula (I). However, the effective ingredient was severely decomposed and destabilized depending on the type of the organic acid to fail in providing a remedy with excellent dissolution property and chemical stability. Then the present inventors intensively studied to find that a chemically stable oral preparation with the improved dissolution property can be obtained by adding thereto a specific organic acid, 1 g of which requires not less than 30 mL water to dissolve in at 20° C., thereby completing the present invention.

That is, the present invention provides an oral preparation comprising an organic acid and as an effective ingredient a morphinan derivative having a nitrogen-containing heterocyclic group represented by the Formula (I):

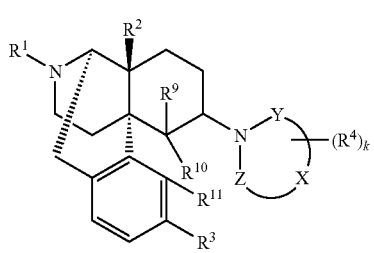

(I)

[wherein $R^1$ is hydrogen, $C_1$-$C_5$ alkyl, $C_4$-$C_7$ cycloalkylalkyl, $C_6$-$C_8$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5); $R^2$ and $R^3$ independently are hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; Y and Z independently represent valence bond or —C(=O)—; —X— represents a $C_2$-$C_7$ carbon chain (one or more of the carbon atoms therein optionally is(are) replaced by nitrogen, oxygen or sulfur atom(s), and the carbon chain optionally contains an unsaturated bond) constituting a part of the ring structure; k is an integer of 0 to 8; $R^4$ is(are) (a) substituent(s) in the number of k on the nitrogen-containing ring, which independently represent(s) fluorine, chlorine, bromine, iodine, nitro, hydroxy, $C_1$-$C_5$ alkyl, $C_7$-$C_{13}$ cycloalkylalkyl, $C_6$-$C_{12}$ aryl, $C_7$-$C_{13}$ aralkyl, $C_7$-$C_{13}$ aralkyloxy, $C_1$-$C_5$ alkoxy, trifluoromethyl, trifluoromethoxy, cyano, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$, or among the $R^4$s in the number of k, two $R^4$s bound to the same carbon atom or to the same sulfur atom together represent one oxygen atom to form carbonyl or sulfoxide (with the proviso that in cases where Y or Z is valence bond, the formed carbonyl is not bound directly to the nitrogen atom which is bound to the morphinan structure), or two $R^4$s bound to the same carbon atom together represent one sulfur atom to form thiocarbonyl, or four $R^4$s bound to the same sulfur atom together represent two oxygen atoms to form sulfone, or among the $R^4$s in the number of k, two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s, wherein $R^5$(s) independently represent(s) fluorine, chlorine, bromine, iodine, nitro, hydroxy, $C_1$-$C_5$ alkyl, $C_1$-$C_5$ alkoxy, trifluoromethyl, trifluoromethoxy, cyano, $C_6$-$C_{12}$ aryl, $C_7$-$C_{13}$ aralkyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$; $R^9$ is hydrogen, $C_1$-$C_5$ alkyl, $C_1$-$C_5$ alkenyl, $C_7$-$C_{13}$ aralkyl, $C_1$-$C_3$ hydroxyalkyl, $(CH_2)_pOR^6$ or $(CH_2)_pCO_2R^6$; $R^{10}$ and $R^{11}$ are bound to form —O—, —S— or —$CH_2$—, or $R^{10}$ is hydrogen and $R^{11}$ is hydrogen, hydroxy, $C_1$-$C_5$ alkoxy or $C_1$-$C_5$ alkanoyloxy; p is an integer of 0 to 5; $R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ independently are hydrogen, $C_1$-$C_5$ alkyl or $C_7$-$C_{13}$ aralkyl]

or a pharmaceutically acceptable acid addition salt thereof, wherein 1 g of said organic acid requires not less than 30 mL of water to dissolve in at 20° C. The present invention also provides a method for improving dissolution property and chemical stability of an oral preparation, which method comprising incorporating an organic acid in said oral preparation comprising as an effective ingredient a morphinan derivative represented by the Formula (I) described above or a pharmaceutically acceptable acid addition salt thereof, wherein 1 g of said organic acid requires not less than 30 mL of water to dissolve in at 20° C.

Effects of the Invention

The oral preparations according to the present invention have a good dissolution property compared to those not comprising an organic acid. By incorporating a specific organic acid, 1 g of which requires not less than 30 mL of water to dissolve in at 20° C., in the oral preparation, destabilization of a morphinan derivative having a nitrogen-containing heterocyclic group represented by the Formula (I) or pharmaceutically acceptable acid addition salt thereof can be avoided, and thus an oral preparation having excellent dissolution property and chemical stability for long term can be obtained.

BRIEF DESCRIPTION OF THE DRAWINGS

FIG. 1 is a graph showing the dissolution property of various tablets described in Formulation Examples 1-3 and Comparative Example 1 which comprise as an effective ingredient a morphinan derivative compound (1) having a nitrogen-containing heterocyclic group. The dissolution ratio (%) of the ingredient is taken along with the ordinate, and the time (min) elapsed from the start of the test is taken along with the abscissa.

BEST MODE FOR CARRYING OUT THE INVENTION

The present invention is an oral preparation comprising a morphinan derivative having a nitrogen-containing heterocyclic group represented by the Formula (I) or a pharmaceutically acceptable acid addition salt thereof as an effective ingredient, and comprising, for the purpose of obtaining chemically stable remedies with a high dissolution property, a specific organic acid, 1 g of which requires not less than 30 mL of water to dissolve in at 20° C.

The compound used as an effective ingredient of the preparation of the present invention is a morphinan derivative having a nitrogen-containing heterocyclic group represented by the Formula (I):

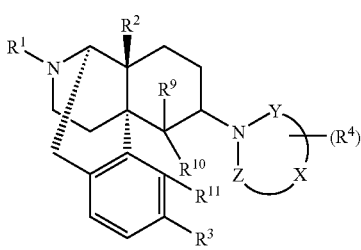

(I)

[wherein $R^1$ is hydrogen, $C_1$-$C_5$ alkyl, $C_4$-$C_7$ cycloalkylalkyl, $C_6$-$C_8$ cycloalkenylalkyl, $C_6$-$C_{19}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5); $R^2$ and $R^3$ independently are hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; Y and Z independently represent valence bond or —C(=O)—; —X— represents a $C_2$-$C_7$ carbon chain (one or more of the carbon atoms therein optionally is(are) replaced by nitrogen, oxygen or sulfur atom(s), and the carbon chain optionally contains an unsaturated bond) constituting a part of the ring structure; k is an integer of 0 to 8; $R^4$ is(are) (a) substituent(s) in the number of k on the nitrogen-containing ring, which independently represent(s) fluorine, chlorine, bromine, iodine, nitro, hydroxy, $C_1$-$C_5$ alkyl, $C_7$-$C_{13}$ cycloalkylalkyl, $C_6$-$C_{12}$ aryl, $C_7$-$C_{13}$ aralkyl, $C_7$-$C_{13}$ aralkyloxy, $C_1$-$C_5$ alkoxy, trifluoromethyl, trifluoromethoxy, cyano, isothiocyanato, $SR^6$, $SOR^E$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$, or among the $R^4$s in the number of k, two $R^4$s bound to the same carbon atom or to the same sulfur atom together represent one oxygen atom to form carbonyl or sulfoxide (with the proviso that in cases where Y or Z is valence bond, the formed carbonyl is not bound directly to the nitrogen atom which is bound to the morphinan structure), or two $R^4$s bound to the same carbon atom together represent one sulfur atom to form thiocarbonyl, or four $R^4$s bound to the same sulfur atom together represent two oxygen atoms to form sulfone, or among the $R^4$s in the number of k, two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s, wherein $R^5$(s) independently represent(s) fluorine, chlorine, bromine, iodine, nitro, hydroxy, $C_1$-$C_5$ alkyl, $C_1$-$C_5$ alkoxy, trifluoromethyl, trifluoromethoxy, cyano, $C_6$-$C_{17}$ aryl, $C_7$-$C_{13}$ aralkyl, isothiocyanato, $SR^6$, $SOR^E$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$; $R^9$ is hydrogen, $C_1$-$C_5$ alkyl, $C_1$-$C_5$ alkenyl, $C_7$-$C_{13}$ aralkyl, $C_1$-$C_3$ hydroxyalkyl, $(CH_2)_pOR^6$ or $(CH_2)_pCO_2R^6$; $R^{10}$ and $R^{11}$ are bound to form —O—, —S— or —$CH_2$—, or $R^{10}$ is hydrogen and $R^{11}$ is hydrogen, hydroxy, $C_1$-$C_5$ alkoxy or $C_1$-$C_5$ alkanoyloxy; p is an integer of 0 to 5; $R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ independently are hydrogen, $C_1$-$C_5$ alkyl or $C_7$-$C_{13}$ aralkyl]
or a pharmaceutically acceptable acid addition salt thereof, which can be produced by the method described in Patent Literature 1.

In the Formula (I), it is preferred that at least one of Y and Z be —C(=O)—, and more preferred that both Y and Z be —C(=O)—.

$R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl. Among these, more preferred are hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, 2-cyclobutenylethyl, 3-cyclobutenylpropyl, phenyl, naphthyl, tolyl, allyl and prenyl. Among these, especially preferred are hydrogen, cyclopropylmethyl, cyclobutylmethyl, cyclopentylmethyl, cyclohexylmethyl, allyl and prenyl.

$R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are especially preferred.

$R^3$ is preferably hydrogen, hydroxy, $C_1$-$C_5$ alkoxy, $C_7$-$C_{13}$ aralkyloxy or $C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred.

The "—X—" is preferably $C_2$-$C_4$ carbon chain constituting a part of the ring structure, more preferably a carbon chain having two carbon atoms constituting a part of the ring structure.

The "k" is preferably an integer of 2 to 6.

$R^4$ is preferably $C_1$-$C_5$ alkyl, $C_1$-$C_{13}$ aralkyl, $C_7$-$C_{13}$ aralkyloxy, or two $R^4$s bound to adjacent carbon atoms, respectively, together form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of the fused rings is non-substituted or substituted by 1 or more $R^5$s. More preferably, $R^4$ is methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy, chlorophenoxy or to form benzene fused ring. Especially preferably, two $R^4$s bound to adjacent carbon atoms, respectively, together form benzene fused ring substituted by 1 or more, preferably 1 to $4R^5$s.

Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^E$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituents $R^5$ selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl and amino.

$R^9$ is preferably hydrogen, $C_1$-$C_5$ alkyl, allyl or benzyl, more preferably hydrogen or methyl.

$R^{10}$ and $R^{11}$ are preferably bound to form —O—, or $R^{10}$ is preferably hydrogen and $R^{11}$ is preferably hydrogen, hydroxy or methoxy. Especially preferably, $R^{10}$ and $R^{11}$ are bound to form —O—.

Especially preferred is the compound wherein $R^1$ is cyclopropylmethyl; $R^2$ and $R^3$ are hydroxy; both Y and Z are —C(═O)—; —X— is a $C_2$ carbon chain constituting a part of the ring structure; two les together form unsubstituted benzene fused ring; $R^9$ is hydrogen; and $R^{10}$ and $R^{11}$ are bound to form —O—, named N-(17-cyclopropylmethyl-4,5α-epoxy-3,14-dihydroxy-morphinan-6β-yl)-phthalimide (hereinafter referred to as Compound (1)).

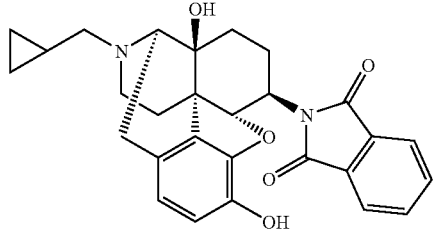

Compound (1)

Preferred examples of the pharmaceutically acceptable acid addition salt of a morphinan derivative having a nitrogen-containing heterocyclic group represented by the Formula (I) include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

Although the administration dose of the oral preparation according to the present invention may be appropriately selected depending on the symptom, age, body weight, administration method and the like, the dose of a morphinan derivative having a nitrogen-containing heterocyclic group or a pharmaceutically acceptable acid addition salt thereof contained as an effective ingredient per adult per day may be 0.1 µg to 10 g, preferably 1 µg to 1 g, and may be administered in one time or dividedly in several times.

The organic acid which can be used in the oral preparation of the present invention may be any pharmaceutically acceptable organic acid as long as 1 g of the organic acid requires not less than 30 mL, preferably not less than 100 mL of water to dissolve in at 20° C. Examples of the organic acid include fumaric acid, L-glutamic acid, L-aspartic acid, phthalic acid, alginic acid, adipic acid, stearic acid, glycyrrhizinic acid, sorbic acid, benzoic acid, and a mixture of two or more of these. Preferred examples include fumaric acid, L-glutamic acid, L-aspartic acid and a mixture of two or more of these.

The organic acid 1 g of which requires not less than 30 mL of water to dissolve in at 20° C. refers to such an organic acid that 30 mL or more of water is required to dissolve 1 g of the organic acid within 30 minutes at 20±5° C. by vigorous shaking for 30 seconds each time at 5-minute intervals, in accordance with the description about solubility in the Japanese Pharmacopoeia, 15th Edition, General Notices, page A-13. Table 1 shows the list of the terms given for solubility in the Japanese Pharmacopoeia, 15th Edition, General Notices, page A-13.

TABLE 1

| Descriptive term | Solvent required for 1 g or 1 mL of solute |
| --- | --- |
| Very soluble | Less than 1 mL |
| Freely soluble | From 1 mL to 10 mL |
| Soluble | From 10 mL to 30 mL |
| Sparingly soluble | From 30 mL to 100 mL |
| Slightly soluble | From 100 mL to 1000 mL |
| Very slightly soluble | From 1000 mL to 10,000 mL |
| Practically insoluble or insoluble | 10,000 mL and over |

The content of the above-described organic acid in the present invention is not restricted, and may be 0.01 to 60% by weight based on the total weight of the oral preparation. If the content is more than 60% by weight, the disintegration property is decreased, which is undesirable to oral preparations. The content of the organic acid is more preferably 0.1 to 40% by weight, especially preferably 1.0 to 20.0% by weight based on the total weight of the oral preparation.

The administration mode is not restricted as long as the preparation is for oral administration, and the preparation may be in any dosage forms such as tablets, capsules, dry syrups, syrups, granules, powders, gels, suspensions, emulsions and the like.

When the preparations are produced, the preparation may contain vehicles, binders, disintegrants, lubricants and the like used in the art as required. The used vehicles and the like are not restricted, and examples of the vehicle include lactose, saccharose, sucrose, sorbitol, mannitol, erythritol, crystalline cellulose, corn starch, gelatin, dextran, and low substituted hydroxypropylcellulose, and examples of the binder include hydroxypropylcellulose, hydroxypropylmethylcellulose, polyvinylpyrrolidone, and methylcellulose. Examples of the disintegrant include starch, crystalline cellulose, low substituted hydroxypropylcellulose, croscarmellose sodium, crospovidone, carmellose calcium, and partially-alphanized starch. Examples of the lubricant include magnesium stearate, calcium stearate, stearic acid, sucrose fatty acid ester, light anhydrous silicic acid, and talc.

For obtaining the oral preparations, direct compression method in which materials are mixed using a drum blender or the like and immediately thereafter tablets are compressed; wet granulation/compression method in which materials are granulated by wet granulation using a high-speed mixer and a fluid bed granulator or the like, and then tablets are compressed; and dry granulation method in which the components are uniformly mixed and then subjected to dry granulation using a roller compactor or the like may be used.

EXAMPLES

The present invention will now be described by way of an example thereof to illustrate excellent effects of the present invention. However, the present invention is not restricted to the examples below.

Example 1

Improvement of Dissolution Property by Addition of Organic Acid

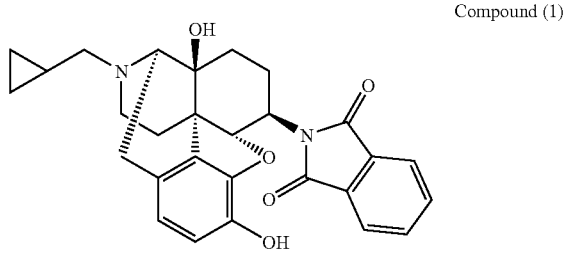 [SMILES: O=C1c2ccccc2C(=O)N1[C@@H]1CC[C@@]2(O)[C@H]3Cc4ccc(O)c5c4[C@@]2(CCN3CC2CC2)[C@H]1O5]

Compound (1)

Formulation Example 1

To 2.0 parts by weight (hereinafter referred to as "part(s)" for short) of the morphinan derivative compound (1) having a nitrogen-containing heterocyclic group, 13.0 parts of fumaric acid as a organic acid (which corresponds to 9.09% by weight of the total contents), 92.25 parts of lactose, 35.1 parts of potato starch and 0.65 part of magnesium stearate were added, and the resultant was well mixed in a mortar. Thereafter 143 mg of the mixture was packed in a punch and die with 7 mmϕ and pressed to make a tablet.

Formulation Example 2

A tablet was made in the same manner as in Formulation Example 1 except that the used fumaric acid is decreased to 6.50 parts (which corresponds to 4.76% by weight of the total contents) and thereby decreasing the total weight of the tablet to 136.50 mg.

Formulation Example 3

A tablet was made in the same manner as in Formulation Example 1 except that the used fumaric acid is decreased to 3.25 parts (which corresponds to 2.44% by weight of the total contents) and thereby decreasing the total weight of the tablet to 133.25 mg.

Comparative Example 1

A tablet was made in the same manner as in Formulation Example 1 except that the total weight of the tablet was decreased to 130 mg by excluding fumaric acid from Formulation Example 1.

(Dissolution Test)

In accordance with the paddle method described in the Japanese Pharmacopoeia, 15th Edition, "Dissolution Test", page B-587, a dissolution test was carried out on the tablets of Formulation Examples 1 to 3 and Comparative Example 1 at 50 rpm using 900 mT of the second fluid of the disintegration test described in the Japanese Pharmacopoeia, 15th Edition, "Reagents, Test Solutions", page B-1012. Dissolution ratio at each time point was measured by HPLC and calculated.

The result is shown in FIG. 1. The dissolution ratio of the tablet of Comparative Example 1, which did not contain any organic acid, was about 40% at the time point of 30 min. On the other hand, the tablets of Formulation Examples 1 to 3, to which fumaric acid was added, showed the increased dissolution ratio. Thus it was confirmed that the dissolution property can be improved by addition of an organic acid.

Example 2

Chemical Stability in Powders

Formulation Example 4

Accurately weighed 2 parts of the morphinan derivative compound (1) having a nitrogen-containing heterocyclic group and lactose, respectively, were mixed in an agate mortar. Then accurately weighed 198 parts of lactose was added in small portions thereto to prepare a mixed powder. To 6 parts of the mixed powder, 12 parts of fumaric acid (which corresponds to 20% by weight of the total contents) and 42 parts of lactose were added, and the resultant was mixed in an agate mortar.

Formulation Example 5

A powder was prepared in the same manner as in Formulation Example 4 except that L-aspartic acid was used instead of fumaric acid.

Formulation Example 6

A powder was prepared in the same manner as in Formulation Example 4 except that L-glutamic acid was used instead of fumaric acid.

Comparative Example 2

To 6 parts of the mixed powder of the morphinan derivative compound (1) having a nitrogen-containing heterocyclic group and lactose prepared in Formulation Example 4, 48 parts of mannitol and 6 parts of lactose were added, and the resultant was mixed in an agate mortar.

Comparative Example 3

To 6 parts of the mixed powder of the morphinan derivative compound (1) having a nitrogen-containing heterocyclic group and lactose prepared in Formulation Example 4, 54 parts of lactose was added, and the resultant was mixed in an agate mortar.

Comparative Example 4

A powder was prepared in the same manner as in Formulation Example 4 except that ascorbic acid was used instead of fumaric acid.

Comparative Example 5

A powder was prepared in the same manner as in Formulation Example 4 except that anhydrous citric acid was used instead of fumaric acid.

Comparative Example 6

A powder was prepared in the same manner as in Formulation Example 4 except that tartaric acid was used instead of fumaric acid.

(Result of Stability Test)

The above-described powders were left to stand for 8 weeks under the accelerated test condition described in Drug Approval and Licensing Procedures in Japan (2006), i.e., the condition of 40° C., 75% relative humidity, and thereafter an amount of the generated decomposition products was measured by HPLC to evaluate the stability. The result is shown in Table 2. In the powders of Comparative Examples 4 to 6, which contained such an organic acid that 1 g of the organic acid dissolves in less than 30 mL of water at 20° C., an amount of decomposition products remarkably increased. On the other hand, in the powders of Formulation Examples 4 to 6, which contained such an organic acid that not less than 30 ml of water is required to dissolve 1 g of the organic acid in at 20° C., an amount of the generated decomposition products was almost the same or less compared to the powders of Comparative Example 2 or 3, which did not contain any organic acid. The result indicates that preparations which contain such an organic acid that not less than 30 mL of water is required to dissolve 1 g of the organic acid in at 20° C. have a good chemical stability as well as an improved dissolution property as shown in Example 1.

Formulation Example 8

A tablet was obtained in the same manner as in Formulation Example 7 except that the used lactose was decreased to 52.67 parts and that 0.13 part of fumaric acid was used. The content of each component converted into % by weight is shown in Table 3.

Formulation Example 9

To 0.1 part of the morphinan derivative compound (1) having a nitrogen-containing heterocyclic group, 118.0 parts of lactose, 68.4 parts of corn starch, 4.5 parts of croscarmellose sodium, 6 parts of hydroxypropylcellulose, 2 parts of benzoic acid as an organic acid, and 1 part of magnesium stearate were added, and the resultant was mixed with a V-blender. Then 200 mg of the resulting mixed powder was packed in a No. 2 gelatin capsule by hand to obtain an encapsulated formulation. The content of each component converted into % by weight is shown in Table 3. An amount of water required to dissolve 1 g of benzoic acid in at 20° C. is from 100 mL to 1000 mL.

Formulation Example 10

To 0.1 part of the morphinan derivative compound (1) having a nitrogen-containing heterocyclic group, 38.1 parts of mannitol, 38.2 parts of lactose, 40.0 parts of low substituted hydroxypropylcellulose, 4.5 parts of croscarmellose sodium, 6.5 parts of fumaric acid as an organic acid, and 0.65 part of magnesium stearate were added, and the resultant was mixed with a V-blender. The resulting mixed powder was granulated by dry granulation and then subjected to size

TABLE 2

|  | Formulation Example 4 | Formulation Example 5 | Formulation Example 6 | Comparative Example 2 | Comparative Example 3 | Comparative Example 4 | Comparative Example 5 | Comparative Example 6 |
| --- | --- | --- | --- | --- | --- | --- | --- | --- |
| Organic acid | Fumaric acid | L-Aspartic acid | L-Glutamic acid | none | none | Ascorbic acid | Anhydrous citric acid | Tartaric acid |
| Water required to dissolve 1 g of organic acid in at 20° C. (mL) | 100 mL or more | 100 mL or more | 100 mL or more |  |  | From 1 mL to 10 mL | Less than 1 mL | Less than 1 mL |
| Amount of decomposition products after being left to stand at 40° C., 75% RH for 8 weeks (%) | 0.46 | 0.85 | 0.80 | 0.43 | 1.28 | 3.90 | 9.76 | 16.5 |

Example 3

Chemical Stability in Tablets and Capsules

Formulation Example 7

To 0.1 part of the morphinan derivative compound (1) having a nitrogen-containing heterocyclic group, 52.787 parts of lactose, 40 parts of potato starch, 30 parts of low substituted hydroxypropylcellulose, 4.5 parts of carboxymethylcellulose calcium, 0.013 part of fumaric acid as an organic acid, and 2.6 parts of magnesium stearate were added, and the resultant was mixed with a V-blender, followed by tableting with a rotary tableting machine to obtain a 130 mg tablet. The content of each component converted into % by weight is shown in Table 3.

selection to obtain granules. To the granules, 1.95 parts of magnesium stearate was added, and the resultant was mixed with a V-blender, followed by tableting with a rotary tableting machine to obtain a 130 mg tablet. The content of each component converted into % by weight is shown in Table 3.

Formulation Example 11

To 0.1 part of the morphinan derivative compound (1) having a nitrogen-containing heterocyclic group, 175.9 parts of lactose, 96 parts of low substituted hydroxypropylcellulose, 32 parts of croscarmellose sodium, and 16 parts of fumaric acid as an organic acid were added, and the resultant was mixed with a V-blender. The resulting mixed powder was granulated by dry granulation and then subjected to size selection, and 320 mg of the obtained granules were packed in No. 1 HPMC capsule by hand to obtain an encapsulated formulation. The content of each component converted into % by weight is shown in Table 3.

Formulation Example 12

To 0.1 part of the morphinan derivative compound (1) having a nitrogen-containing heterocyclic group, 76.3 parts of lactose, 40 parts of low substituted hydroxypropylcellulose, 4.5 parts of croscarmellose sodium, 6.5 parts of L-glutamic acid as an organic acid, and 2.6 parts of magnesium stearate were added, and the resultant was mixed with a V-blender, followed by tableting with a rotary tableting machine to obtain a 130 mg tablet. The content of each component converted into % by weight is shown in Table 3.

Formulation Example 13

A tablet was obtained in the same manner as in Formulation Example 12 except that the used lactose was decreased to 62.8 parts and that 20 parts of fumaric acid was used instead of L-glutamic acid. The content of each component converted into % by weight is shown in Table 3.

Formulation Example 14

A tablet was obtained in the same manner as in Formulation Example 7 except that the used lactose was decreased to 0.8 part and that 52 parts of fumaric acid was used. The content of each component converted into % by weight is shown in Table 3.

Formulation Example 15

A tablet was obtained in the same manner as in Formulation Example 7 except that lactose was not added, that the used potato starch was decreased to 14.8 parts, and that 78 parts of fumaric acid was used. The content of each component converted into % by weight is shown in Table 3.

Comparative Example 7

A tablet was obtained in the same manner as in Formulation Example 12 except that 6.5 parts of anhydrous citric acid was added as an organic acid instead of L-glutamic acid. The content of each component converted into % by weight is shown in Table 3.

Comparative Example 8

An encapsulated formulation was obtained in the same manner as in Formulation Example 9 except that the used lactose was decreased to 100 parts and that 20 parts of ascorbic acid was added as an organic acid instead of benzoic acid. The content of each component converted into % by weight is shown in Table 3.

Comparative Example 9

An encapsulated formulation was obtained in the same manner as in Formulation Example 9 except that the used lactose was decreased to 60 parts and that 60 parts of succinic acid was added as an organic acid instead of benzoic acid. The content of each component converted into % by weight is shown in Table 3. An amount of water required to dissolve 1 g of succinic acid in at 20° C. was 10 mL.

(Result of Stability Test)

As carried out in Example 2, the obtained tablets and capsules were left to stand for 4 weeks under the accelerated test condition described in Drug Approval and Licensing Procedures in Japan (2006), i.e., the condition of 40° C., 75% relative humidity, and thereafter an amount of the generated decomposition products was measured. The result is shown in Table 3. The preparations of Formulation Examples 7 to 15, which contained such an organic acid that not less than 30 mL of water is required to dissolve 1 g of the organic acid in at 20° C., had smaller amount of decomposition products and good chemical stability compared to the preparations of Comparative Examples 7 to 9, which contained such an organic acid that 1 g of the organic acid dissolves in less than 30 mL of water at 20° C.

TABLE 3

| | Content (% by weight) | | | | | | | | | | | |
|---|---|---|---|---|---|---|---|---|---|---|---|---|
| | Formulation Example 7 | Formulation Example 8 | Formulation Example 9 | Formulation Example 10 | Formulation Example 11 | Formulation Example 12 | Formulation Example 13 | Formulation Example 14 | Formulation Example 15 | Comparative Example 7 | Comparative Example 8 | Comparative Example 9 |
| Dosage form | Tablet | Tablet | Capsule | Tablet | Capsule | Tablet | Tablet | Tablet | Tablet | Tablet | Capsule | Capsule |
| Compound (I) | 0.08 | 0.08 | 0.05 | 0.08 | 0.03 | 0.08 | 0.08 | 0.08 | 0.08 | 0.08 | 0.05 | 0.05 |
| Mannitol | — | — | — | 29.3 | — | — | — | — | — | — | — | — |
| Lactose | 40.6 | 40.5 | 59.0 | 29.4 | 55.0 | 58.7 | 48.3 | 0.6 | — | 58.7 | 50.0 | 30.0 |
| Corn starch | — | — | 34.2 | — | — | — | — | — | — | — | 34.2 | 34.2 |
| Potato starch | 30.8 | 30.8 | — | — | — | — | — | 30.8 | 11.4 | — | — | — |
| Low substituted hydroxypropylcellulose | 23.1 | 23.1 | — | 30.8 | 30.0 | 30.8 | 30.8 | 23.1 | 23.1 | 30.8 | — | — |
| Croscarmellose sodium | — | — | 2.25 | 3.5 | 10.0 | 3.5 | 3.5 | — | — | 3.5 | 2.25 | 2.25 |
| Hydroxypropylcellulose | — | — | 3.0 | — | — | — | — | — | — | — | 3.0 | 3.0 |
| Carboxymethylcellulose calcium | 3.5 | 3.5 | — | — | — | — | — | 3.5 | 3.5 | — | — | — |
| Fumaric acid | 0.01 | 0.1 | — | 5.0 | 5.0 | — | 15.4 | 40.0 | 60.0 | — | — | — |
| L-Glutamic acid | — | — | — | — | — | 5.0 | — | — | — | — | — | — |
| Benzoic acid | — | — | 1.0 | — | — | — | — | — | — | — | — | — |
| Anhydrous citric acid | — | — | — | — | — | — | — | — | — | 5.0 | — | — |
| Ascorbic acid | — | — | — | — | — | — | — | — | — | — | 10.0 | — |
| Succinic acid | — | — | — | — | — | — | — | — | — | — | — | 30.0 |
| Magnesium stearate | 2.0 | 2.0 | 0.5 | 2.0 | — | 2.0 | 2.0 | 2.0 | 2.0 | 2.0 | 0.5 | 0.5 |
| Amount of decomposition product generated after being left for 4 weeks at 40° C., 75% RH (%) | 0.44 | 0.43 | 0.28 | 0.42 | 0.49 | 0.45 | 0.26 | 0.35 | 0.36 | 0.76 | 1.21 | 0.85 |

Example 4

Effect of Addition of Fumaric Acid on Chemical Stability and Dissolution Property of Tablets Formulation Example 16

To 3 parts of the morphinan derivative compound (1) having a nitrogen-containing heterocyclic group, 35.2 parts of mannitol, 38.2 parts of lactose, 40.0 parts of low substituted hydroxypropylcellulose, 4.5 parts of croscarmellose sodium, 6.5 parts of fumaric acid as an organic acid, and 0.65 part of magnesium stearate were added, and the resultant was mixed with a V-blender. The resulting mixed powder was granulated by dry granulation and then subjected to size selection to obtain granules. To the granules, 1.95 parts of magnesium stearate was added, and the resultant was mixed with a V-blender, followed by tableting with a rotary tableting machine to obtain a 130 mg tablet. The content of each component converted into % by weight is shown in Table 4.

Comparative Example 10

A tablet was prepared in the same manner as in Formulation Example 16 except that 6.5 parts of fumaric acid was excluded from Formulation Example 16 and that the used mannitol was increased from 35.2 parts to 41.7 parts.

(Result of Stability Test)

As carried out in Example 2, the tablets of Formulation Example 16 and Comparative Example 10 were left to stand for 4 weeks under the accelerated test condition described in Drug Approval and Licensing Procedures in Japan (2006), i.e., the condition of 40° C., 75% relative humidity, and thereafter an amount of the generated decomposition products was measured. The result is shown in Table 4. The tablet of Formulation Example 16, which contained fumaric acid which is such an organic acid that not less than 30 mL of water is required to dissolve 1 g of the organic acid in at 20° C., had a good chemical stability and no problem in quality, generating slightly more decomposition products compared to the tablet of Comparative Example 10 which did not contain fumaric acid.

(Result of Dissolution Test)

As carried out in Example 1, in accordance with the paddle method described in the Japanese Pharmacopoeia, 15th Edition, "Dissolution Test", page B-587, a dissolution test was carried out on the tablets of Formulation Example 16 and Comparative Example 10 at 50 rpm using 900 mL of the second fluid of the disintegration test described in the Japanese Pharmacopoeia, 15th Edition, "Reagents, Test Solutions", page B-1012.

The result is shown in Table 4. While the tablet of Comparative Example 10 not containing any organic acid had such an incomplete dissolution property that the dissolution ratio at 30 min was 88%, the tablet of Formulation Example 16 containing 5% fumaric acid achieved more than 95% dissolution at 15 min and complete dissolution within 30 min, confirming that the dissolution property is improved by fumaric acid.

The above-described results indicate that, compared to the preparation of Comparative Example 10 not containing fumaric acid, the preparation of Formulation Example 16 containing fumaric acid which is such an organic acid that not less than 30 mL of water is required to dissolve 1 g of the organic acid in at 20° C. has an excellent dissolution property and no problem in shelf stability, and thus achieves both the dissolution property and chemical stability.

TABLE 4

Content (% by weight)

| | | Formulation Example 16 | Comparative Example 10 |
|---|---|---|---|
| Dosage form | | Tablet | Tablet |
| Compound (I) | | 2.31 | 2.31 |
| Mannitol | | 27.08 | 32.08 |
| Lactose | | 29.38 | 29.38 |
| Low substituted hydroxypropylcellulose | | 30.77 | 30.77 |
| Croscarmellose sodium | | 3.46 | 3.46 |
| Fumaric acid | | 5.0 | — |
| Magnesium stearate | | 2.0 | 2.0 |
| Amount of decomposition product generated after being left for 4 weeks at 40° C., 75% RH (%) | | 0.37 | 0.35 |
| Result of dissolution test on tablets immediately after tableting using second fluid of disintegration test described in the Japanese Pharmacopoeia, Time course of release ratio (%) | 7.5 min | 89 | 63 |
| | 15 min | 96 | 77 |
| | 30 min | 100 | 88 |

The invention claimed is:

1. An oral preparation comprising an organic acid and as an effective ingredient the compound N-(17-cyclopropylmethyl-4,5α-epoxy-3,14-dihydroxy-morphinan-6β-yl)-phthalimide or a pharmaceutically acceptable acid addition salt thereof, wherein said organic acid is one selected from the group consisting of fumaric acid, L-glutamic acid, L-aspartic acid and benzoic acid, or a mixture of two or more of these, and the organic acid is 0.01 to 60% by weight based on a total weight of the oral preparation.

2. The oral preparation according to claim 1, wherein said organic acid is fumaric acid.

3. The oral preparation according to claim 1, which is a tablet, capsule or powder.

4. A method for improving dissolution property and chemical stability of an oral preparation, which method comprising incorporating an organic acid in the oral preparation comprising as an effective ingredient the compound recited in claim 1 or a pharmaceutically acceptable acid addition salt thereof, wherein said organic acid is one selected from the group consisting of fumaric acid, L-glutamic acid, L-aspartic acid and benzoic acid, or a mixture of two or more of these, and the organic acid is 0.01 to 60% by weight based on a total weight of the oral preparation.

5. The method according to claim 4, wherein said organic acid is fumaric acid.

6. The method according to claim 4, wherein said oral preparation is a tablet, capsule or powder.

* * * * *